(12) United States Patent
Park et al.

(10) Patent No.: US 12,070,332 B2
(45) Date of Patent: Aug. 27, 2024

(54) WEARABLE DEVICE AND METHOD OF CALIBRATING FORCE SENSOR IN WEARABLE DEVICE

(71) Applicant: SAMSUNG ELECTRONICS CO., LTD., Suwon-si (KR)

(72) Inventors: Sang Yun Park, Hwaseong-si (KR); Jae Min Kang, Seoul (KR); Byung Hoon Ko, Hwaseong-si (KR); Seung Woo Noh, Seongnam-si (KR); Jin Woo Choi, Ansan-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 306 days.

(21) Appl. No.: 17/748,557

(22) Filed: May 19, 2022

(65) Prior Publication Data

US 2023/0200731 A1    Jun. 29, 2023

(30) Foreign Application Priority Data

Dec. 23, 2021    (KR) .......................... 10-2021-0186036

(51) Int. Cl.
*A61B 5/00* (2006.01)
*A61B 5/021* (2006.01)
*G06F 1/16* (2006.01)

(52) U.S. Cl.
CPC .......... *A61B 5/681* (2013.01); *A61B 5/02108* (2013.01); *A61B 5/6843* (2013.01); *G06F 1/163* (2013.01); *A61B 2562/0247* (2013.01)

(58) Field of Classification Search
CPC .......... A61B 5/389; A61B 34/30; A61B 34/37; A61B 5/01; A61B 5/681; A61B 2090/064; A61B 5/4851; A61B 5/6811; A61B 17/3468; A61B 5/0205; A61B 5/14532; A61B 17/1128; A61B 18/0206; A61B 18/0218; A61B 2017/00477; A61B 2018/046; A61B 2560/0219; A61B 34/25; A61B 5/0015; A61B 5/0031; A61B 5/067; A61B 5/24; A61B 5/686; A61B 2562/0219; A61B 34/20; A61B 5/002; A61B 5/1118; A61B 5/6807; A61B 90/37; A61B 90/50; A61B 2034/2051; A61B 34/32;

(Continued)

(56) References Cited

U.S. PATENT DOCUMENTS

| 7,176,897 B2 | 2/2007 | Roberts |
| 7,784,366 B2 | 8/2010 | Daverman et al. |

(Continued)

FOREIGN PATENT DOCUMENTS

| KR | 10-1566571 B1 | 11/2015 |
| KR | 10-1809081 B1 | 1/2018 |
| KR | 10-1905046 B1 | 10/2018 |
| KR | 10-2007073 B1 | 8/2019 |

*Primary Examiner* — Andre J Allen
(74) *Attorney, Agent, or Firm* — Sughrue Mion, PLLC

(57) ABSTRACT

A wearable device includes a main body, a force sensor disposed on one surface of the main body and configured to measure a force, and a processor configured to control the force sensor to measure a first force when the one surface of the main body faces upwards, control the force sensor to measure a second force sensor when the one surface of the main body faces downward, and calibrate the force sensor based on at least one of the measured first force and the measured second force.

20 Claims, 13 Drawing Sheets

(58) Field of Classification Search
CPC .............. A61B 2034/301; A61B 34/76; A61B 5/112; A61B 2034/2059; A61B 34/35; A61B 90/361; A61B 2034/302; A61B 2562/0247; A61B 34/74; A61B 1/307; A61B 2034/105; A61B 2034/2048; A61B 2034/2061; A61B 2034/2072; A61B 2034/303; A61B 2090/061; A61B 2090/306; A61B 2090/309; A61B 2090/3614; A61B 2090/376; A61B 2090/3762; A61B 34/70; A61B 5/02108; A61B 5/1176; A61B 5/375; A61B 17/07207; A61B 17/1155; A61B 2017/00017; A61B 2017/00022; A61B 2017/00026; A61B 2017/00119; A61B 2017/00199; A61B 2017/00221; A61B 2017/00398; A61B 2017/07285; A61B 2034/254; A61B 2090/066; A61B 2090/0808; A61B 5/0053; A61B 90/90; A61B 1/045; A61B 17/320068; A61B 17/320092; A61B 18/00; A61B 18/1206; A61B 18/14; A61B 18/1442; A61B 18/1445; A61B 2017/00039; A61B 2017/00044; A61B 2017/00084; A61B 2017/00123; A61B 2017/00225; A61B 2017/00393; A61B 2017/00442; A61B 2017/00464; A61B 2017/00818; A61B 2017/07257; A61B 2017/07271; A61B 2017/07278; A61B 2017/2927; A61B 2017/320074; A61B 2017/320093; A61B 2018/00541; A61B 2018/00595; A61B 2018/00601; A61B 2018/00607; A61B 2018/00613; A61B 2018/0063; A61B 2018/00642; A61B 2018/00827; A61B 2018/00875; A61B 2018/00892; A61B 2018/00982; A61B 2018/00994; A61B 2018/126; A61B 2018/1273; A61B 2034/304; A61B 2034/305; A61B 2090/0811; A61B 2090/3945; A61B 2090/3975; A61B 2217/005; A61B 2217/007; A61B 2218/002; A61B 2218/007; A61B 2218/008; A61B 34/77; A61B 5/02225; A61B 5/02416; A61B 5/02427; A61B 5/02438; A61B 90/30; A61B 90/53; A61B 2017/00738; A61B 2034/742; A61B 2090/372; A61B 2090/502; A61B 2090/508; A61B 34/00; A61B 5/021; A61B 5/4833; A61B 5/6898; A61B 2505/09; A61B 2560/0266; A61B 34/71; A61B 46/10; A61B 5/0022; A61B 90/98; A61B 2560/0462; A61B 5/0059; A61B 5/1121; A61B 5/224; A61B 5/4528; A61B 5/4538; A61B 5/6843; A61B 5/6895; A61B 5/7405; A61B 5/746; A61B 2560/0223; A61B 5/0008; A61B 5/0088; A61B 5/02007; A61B 5/022; A61B 5/107; A61B 5/6844; A61B 5/721; A61B 7/005; A61B 7/006; A61B 7/023; A61B 90/00; A61B 2017/00128; A61B 2017/00473; A61B 2017/00486; A61B 2017/00809; A61B 2017/347; A61B 2034/2055; A61B 2034/2065; A61B 2034/256; A61B 2034/258; A61B 2090/037; A61B 2090/0804; A61B 2090/0805; A61B 2090/0807; A61B 2560/0443; A61B 2560/063; A61B 2562/0261; A61B 2562/166; A61B 5/00; A61B 5/0004; A61B 5/0245; A61B 5/0261; A61B 5/0295; A61B 5/0816; A61B 5/1125; A61B 5/1128; A61B 5/14503; A61B 5/14551; A61B 5/14552; A61B 5/225; A61B 5/486; A61B 5/6823; A61B 5/6826; A61B 5/6849; A61B 5/6887; A61B 5/7221; A61B 90/57; G06F 2203/04105; G06F 3/016; G06F 3/0447; G06F 3/0412; G06F 3/0414; G06F 3/044; G06F 3/0416; G06F 1/1684; G06F 13/4282; G06F 2203/04106; G06F 11/30; G06F 15/00; G06F 1/163; G06F 3/041; G06F 3/0488; G06F 3/04166; G06F 21/32; G06F 3/04883; G06F 3/015; G06F 3/0202; G06F 3/03547; G06F 3/0487; G06F 1/1637; G06F 1/1643; G06F 1/1656; G06F 1/1686; G06F 1/1698; G06F 3/014; G06F 3/0346; G06F 3/0482; G06F 1/169; G06F 3/04144; G06F 1/1662; G06F 3/011; G06F 3/012; G06F 3/0418; G06F 1/1616; G06F 1/1652; G06F 3/04142; G06F 3/0445; G06F 3/045; G06F 3/048; G06F 3/04817; G06F 3/0483; G06F 3/0485; G06F 3/04886; G06F 1/1626; G06F 1/1633; G06F 21/71; G06F 21/83; G06F 2203/04102; G06F 2203/04103; G06F 2203/04809; G06F 3/0362; G06F 3/0484; G06F 3/04845; G06F 3/04847; G06F 1/1677; G06F 1/1679; G06F 1/1694; G06F 2203/04111; G06F 3/0213; G06F 3/0236; G06F 3/03; G06F 3/042; G06F 3/046; G06F 3/14; G06F 3/147; G06F 1/16; G06F 1/1658; G06F 21/12; G06F 21/30; G06F 2203/04104; G06F 3/01; G06F 3/02; G06F 3/0334; G06F 3/03543; G06F 3/043; G06F 3/0443; G06F 9/44; G06F 1/1635; G06F 1/1666; G06F 1/1681; G06F 1/1688; G06F 1/203; G06F 2200/202; G06F 2203/013; G06F 2203/014; G06F 2203/04803; G06F 3/005; G06F 3/017; G06F 3/0216; G06F 3/0233; G06F 3/038; G06F 3/04164; G06F 3/0446; G06F 3/0481; G06F 3/04855; G06F 3/167; G06F 40/166

See application file for complete search history.

(56) References Cited

U.S. PATENT DOCUMENTS

| | | | |
|---|---|---|---|
| 8,169,332 | B2 | 5/2012 | Son |
| 9,262,002 | B2 | 2/2016 | Momeyer et al. |
| 9,459,746 | B2 | 10/2016 | Rosenberg et al. |
| 10,039,455 | B2 | 8/2018 | Lading et al. |
| 10,162,452 | B2 | 12/2018 | Westerman et al. |
| 10,386,970 | B2 | 8/2019 | Harley et al. |
| 10,503,216 | B2 | 12/2019 | Weldon et al. |
| 2020/0008693 | A1 | 1/2020 | Mukkamala et al. |
| 2021/0108975 | A1* | 4/2021 | Peso Parada ......... G01L 5/0038 |
| 2023/0023401 | A1* | 1/2023 | Heo ................. G06F 3/041 |
| 2024/0099419 | A1* | 3/2024 | Gupta ................ A43B 17/00 |

\* cited by examiner

WEARABLE DEVICE AND METHOD OF CALIBRATING FORCE SENSOR IN WEARABLE DEVICE

CROSS-REFERENCE TO RELATED APPLICATION(S)

This application claims the benefit under 35 USC § 119(a) of Korean Patent Application No. 10-2021-0186036, filed on Dec. 23, 2021, in the Korean Intellectual Property Office, the disclosure of which is incorporated herein by reference in its entirety.

BACKGROUND

1. Field

Apparatuses and methods consistent with example embodiments relate to a wearable device for estimating bio-information and a method of calibrating a force sensor in the wearable device.

2. Description of Related Art

Recently, a technology for non-invasive analysis of various components of an object, particularly human tissues, using a force sensor has been developed. Sensors for measuring a force applied to a smart device may include a capacitive sensor, an inductive sensor, a strain gauge, and the like. In general, a force sensor may measure a force by measuring a strain of the sensor under a force applied to the sensor by a user. The force sensor that measures a force in this way may be subjected to deformation over time, and accordingly the accuracy of the sensor is lowered, which may lead to a decrease in the accuracy of estimation of bio-information.

SUMMARY

According to an aspect of the disclosure, a wearable device may include: a main body; a force sensor disposed on one surface of the main body and configured to measure a force; and a processor configured to control the force sensor to measure a first force when the one surface of the main body faces upwards, control the force sensor to measure a second force when the one surface of the main body faces downward, and calibrate the force sensor based on at least one of the measured first force and the measured second force.

The wearable device may further include a display configured to output a first image of the main body with the one surface facing upward, wherein the processor is further configured to control the force sensor to measure the first force while the first image is displayed.

The wearable device may further include a display configured to output a second image of the main body with the one surface facing downward, wherein the processor is further configured to control the force sensor to measure the second force while the second image is displayed.

The processor may be further configured to guide a user such that the one surface of the main body faces upward so as to measure the first force, and guide the user such that the one surface of the main body faces downward so as to measure the second force, by using a display or a speaker of another device wirelessly connected to the wearable device.

When at least one of the first force and the second force, or a statistical value of the first force and the second force is outside a preset reference range, the processor may be further configured to guide a user to re-measure the force or to inspect the wearable device.

When at least one of the first force and the second force or a statistical value of the first force and the second force is not outside a preset reference range, the processor may be further configured to use a preset initial value or update the initial value to at least one of the first force and the second force or the statistical value of the first force and the second force.

The main body may further include a pulse wave sensor disposed on the one surface of the main body and configured to measure a pulse wave signal, and when a contact force and the pulse wave signal are measured by the force sensor and the pulse wave sensor, respectively, at a time of estimating blood pressure, the processor may be further configured to estimate blood pressure based on the contact force and the pulse wave signal.

The processor may be further configured to obtain an oscillometric envelope based on the contact force and the pulse wave signal and to estimate the blood pressure using the oscillometric envelope.

According to another aspect of the disclosure, a wearable device may include: a force sensor configured to measure a force; and a processor configured to control the force sensor to measure a first force value when the wearable device is connected to a charging dock, and calibrate the force sensor based on the first force value measured according to a change in current while the force sensor is connected to the charging dock.

The processor may be further configured to control the force sensor to measure a second force value while the wearable device is not connected to the charging dock and a contact surface of the force sensor faces upward, and to calibrate the force sensor based on the first force value and the second force value.

The wearable device may further include a display configured to output an image of the charging dock being connected to the wearable device.

The processor may be further configured to guide a user to connect the charging dock to the wearable device by using a display or a speaker of another device wirelessly connected to the wearable device.

The wearable device may further include a control circuit configured to control a current in the charging dock, and the processor is further configured to calibrate the force sensor based on a plurality of force values measured for each level of the current according to the current adjusted stepwise to a plurality of levels by the control circuit.

When at least one of the plurality of force values which are measured according to the change in the current, or a statistical value of the plurality of force values, is outside a preset reference range, the processor may be further configured to guide a user to re-measure the force or to inspect the wearable device.

When at least one of a plurality of forces values measured according to the change in the current, or a statistical value of the plurality of force values, is not outside a preset reference range, the processor may be further configured to use a preset initial value or update the preset initial value to at least one of the plurality of force values measured according to the change in the current, or to the statistical value of the plurality of force values.

The wearable device may further include a pulse wave sensor configured to measure a pulse wave signal, and when a contact force and the pulse wave signal are measured by the force sensor and the pulse wave sensor, respectively, at a time of estimating blood pressure, the processor may be further configured to estimate blood pressure based on the contact force and the pulse wave signal.

According to another aspect of the disclosure, a method of calibrating a force sensor in a wearable device, may include: guiding a user to place one surface of a main body to face upwards when the force sensor measures a first force; guiding the user to place the one surface of the main body to face downward when the force sensor measures a second force; and calibrating the force sensor based on at least one of the measured first force and the measured second force.

The guiding the user to place the one surface of the main body to face upwards may include outputting an image of the main body with the one surface facing upward while the force sensor measures the first force.

The guiding of the user to place the one surface of the main body to face downward may include outputting an image of the main body with the one surface facing downward while the force sensor measures the second force.

The calibrating of the force sensor may include guiding the user to re-measure a force or to inspect the wearable device when at least one of the first force and the second force, or a statistical value of the first force and the second force, is outside a preset reference range.

Figure 1:
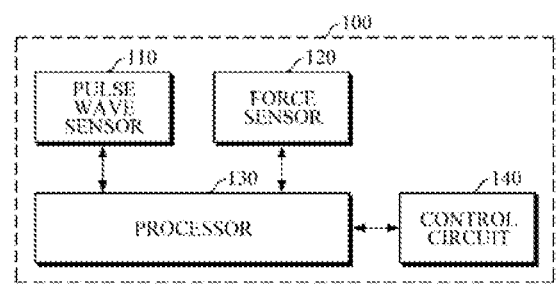
FIG. 1 is a block diagram illustrating a wearable device according to an exemplary embodiment.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

Example embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the example embodiments. However, it is apparent that the example embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the word "comprise" and variations such as "comprises" or "comprising," will be understood to imply the inclusion of stated elements but not the exclusion of any other elements. Terms such as "unit" and "module" denote units that process at least one function or operation, and they may be implemented by using hardware, software, or a combination of hardware and software.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, all of a, b, and c, or any variations of the aforementioned examples.

Hereinafter, embodiments of a wearable device and a method of calibrating a force sensor of the wearable device will be described in detail with reference to the accompanying drawings.

FIG. 1 is a block diagram illustrating a wearable device according to an exemplary embodiment. Referring to FIG. 1, a wearable device 100 may include a pulse wave sensor 110, a force sensor 120, a processor 130, and a control circuit 140.

A wearable device 100 refers to a device that enables a user to freely use both hands without holding the device in his/her hand, and examples of the wearable device 100 may include a wristwatch type, a wristband type, a ring-type, a belt-type, a necklace type, an ankle-band type, a thigh-band type, a forearm band type, and the like. However, the wearable device is not limited to the above examples. The wearable device may estimate blood pressure among various types of bio-information. The bio-information may include, for example, heart rate, vascular age, arterial stiffness, aortic artery pressure waveform, vascular elasticity, stress index, fatigue level, skin elasticity, and sink age, but is not limited thereto. Hereinafter, for convenience of description, a description will be given of an example of estimation of blood pressure.

The pulse wave sensor 110 and the force sensor 120 may obtain data for estimating blood pressure from an object, for example, a photoplethysmography (PPG) signal and a contact force, and the processor 130 may estimate blood pressure of the object by using the obtained data. The processor 130 may be electrically connected to the pulse wave sensor 110 and the force sensor and may control the pulse wave sensor 110 and the force sensor 120 when a request for estimating blood pressure is received. The object may be an area of the human body which can be in contact with the pulse wave sensor 110 and the force sensor, and from which, for example, pulse waves can be easily measured. For example, the object may be a finger which has a high density of blood vessels, but is not limited thereto. The object may be a region of a wrist surface adjacent to the radial artery which is an upper area of the wrist through which capillary blood or venous blood passes, or may be a distal body portion of the human body, such as a toe.

The pulse wave sensor 110 may measure a pulse wave signal including a PPG signal from the object. The pulse wave sensor 110 may be formed by a plurality of channels. Each channel may include one or more light sources configured to emit light of one or more wavelengths, and may be disposed at different positions to enable measurement of pulse wave signals from different positions of the object. In addition, each channel of the pulse wave sensor 110 may include one or more detectors configured to detect the light returning to the detector after being emitted by the light source of each channel and then being scattered, reflected, or transmitted by the biological tissue of the object, such as the skin surface or blood vessel of the object. The detector may include a phototransistor (PTr), an image sensor (e.g., a complementary metal oxide semiconductor (CMOS) image sensor), etc., but is not limited thereto.

When a user gradually increases force pressing the pulse wave sensor 110 while contacting the object with the pulse wave sensor 110, or when a user gradually decreases force after applying a force greater than or equal to a threshold, the force sensor 120 may measure the force acting on the pulse wave sensor 110. The force sensor 120 may be disposed on an upper portion or a lower portion of the pulse wave sensor 110. The force sensor 120 may include a strain gauge, and may be configured as a single force sensor or an array of force sensors. In this case, the force sensor 120 may be transformed into a pressure sensor in which the force sensor 120 and an area sensor are combined, a pressure sensor in the form of an air bag, a force matrix sensor capable of measuring a force for each pixel, or the like.

Figure 5:
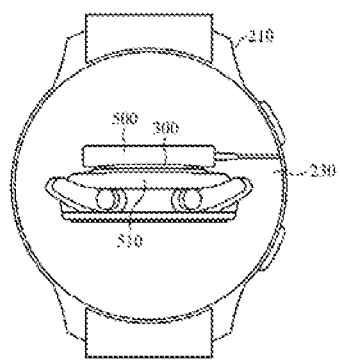
FIG. 5 is a diagram illustrating an example of providing guide in the form of an image to connect a wearable device and a charging dock according to another exemplary embodiment.

The control circuit 141 may control current that flows in a wireless charger (e.g., a wireless charging dock 500 illustrated in FIG. 5). For example, the control circuit 141 may adjust an alternating current flowing in the wireless charger 140 to a plurality of levels and form a magnetic field for each level. When the wearable device 100 and the wireless charger are connected, the control circuit 141 may allow a user to adjust the level of the alternating current. When a connection between the wireless device 100 and the wireless charger 140 is detected, the control circuit 141 may automatically control the alternating current.

Figure 2:
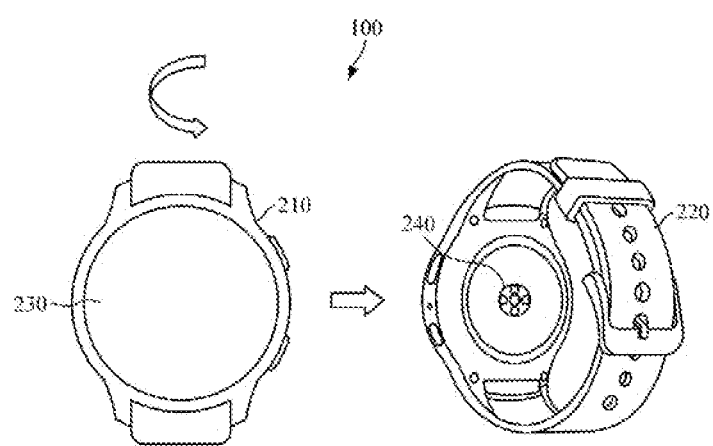
FIG. 2 is a diagram illustrating a watch type wearable device according to an exemplary embodiment.

FIG. 2 is a diagram illustrating a smartwatch type wearable device as an embodiment of the wearable device 100.

Referring to FIG. 2, the wearable device 100 may include a main body 210 and a strap 220. The main body 210 may include a processor 130 and form the outer appearance of the wearable device 100. Also, the main body 210 may further include an output interface. The output interface may output various types of information including time information, received message information, blood pressure information, and the like through a display device 230 on the front side thereof as illustrated. In addition, a sensor module 240 including the pulse wave sensor 110 and the force sensor 120 may be disposed on a rear surface of the main body 210.

The processor 130 may perform calibration of the force sensor 120 in order to measure the accuracy of estimation of blood pressure. For example, the processor 130 may calibrate the force sensor 120 based on a state in which no force is applied to the wearable device and the own weight of the wearable device in the state in which no force is applied.

In general, when the estimation of bio-information is repeated, a force sensor may be subjected to deformation due to the contact with the object. In addition, degradation of performance may occur due to changes in the measurement environment, for example, internal heat generation of a main body, changes in ambient temperature, and the like, which may cause a reduction in the accuracy of measurement of bio-information. Therefore, a method of easily calibrating a force sensor is necessary for accurate force measurement.

Figure 3A:
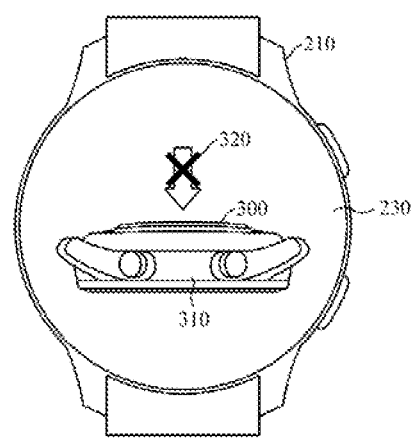
FIGS. 3A and 3B are diagrams illustrating an example of providing guide in the form of an image according to an exemplary embodiment.

First, the processor 130 may guide the user such that the rear surface of the main body 210 on which the force sensor 120 is disposed faces upward so that the force sensor 120 can measure a first force in a state where no force is applied by the object. For example, the processor 130 may output a main body image of the main body 210 with the rear surface facing upward through a display device 230 of the output interface. FIG. 3A is a diagram illustrating an example in which the processor 130 provides guide in the form of an image to measure a first force. FIG. 3A illustrates an image 310 in which the main body is turned over so that a front surface of the main body on which the display device 230 is disposed faces downward and a rear surface 300 on which the force sensor is disposed faces upward, and in this case, as illustrated, an object (e.g., image, text, etc.) 320 instructing the object not to apply force may be displayed. The user may position the main body according to the guide in the form of an image, and accordingly, the force sensor 120 may measure the first force. In addition, in order to increase the accuracy of measurement of force by excluding other forces, accessories of the wearable device, for example, a watch case, a strap, and other accessories connected to the main body, may be removed, and the processor 130 may additionally guide the removal of such accessories.

Figure 3B:
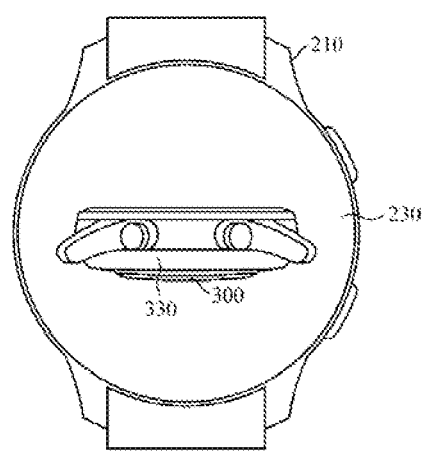

Then, the processor 130 may guide the user such that the rear surface 300 of the main body on which the force sensor 120 is disposed faces downward so that the force sensor 120 can measure a second force by using the own weight of the wearable device in a state in which no force is applied by the object. For example, the processor 130 may output a main body image of the main body with the rear surface facing downward through the display device 230 of the output interface. FIG. 3B is a diagram illustrating an example in which the processor 130 provides guide in the form of an image to measure the second force. FIG. 3B illustrates an image 330 in which a rear surface 300 of the main body on which the display device 230 is disposed faces downward. The user may position the main body according to the guide in the form of an image, and accordingly, the force sensor 120 may measure the second force by using the weight of the wearable device. In addition, as in the measurement of the first force, in order to increase the accuracy of measurement of force by excluding other forces, accessories of the wearable device, for example, a watch case, a strap, and other accessories connected to the main body, may be removed, and the processor 130 may additionally guide the removal of such accessories.

Also, the processor 130 may provide the guide using various methods, such as text messages, voice signals, haptic signals, and the like, as well as the method of using the image through the display device 230. For example, the processor 130 may output a text message or a voice message such as "Please remove the watch strap and turn the main body over," "Please remove the watch strap and place the main body on a flat surface," or the like through the display device 230 of the wearable device. In addition, the processor 130 may also provide guide by, for example, outputting an image of measurement of the first force after one vibration, or outputting an image of measurement of the second force after two vibrations, by using both the image and haptic signals.

Figure 4:
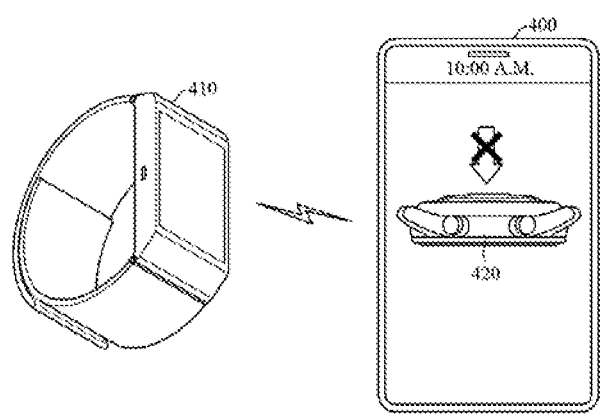
FIG. 4 is a diagram illustrating an example of providing guide via a combination of a wearable device and a smartphone according to an exemplary embodiment.

FIG. 4 is a diagram illustrating an example of providing guide via a combination of a wearable device and a smartphone according to an exemplary embodiment.

As illustrated, the processor may guide the user such that the rear surface of a main body faces upward so as to measure the first force, and may guide the user such that the rear surface of the main body faces downward so as to measure the second force by using a display or a sound output device of another device wirelessly connected to the wearable device. Referring to FIG. 4, a processor may be mounted in a main body of a smartphone 400. Upon receiving a calibration request, the processor of the smartphone 400 may communicate with a communication interface included in the main body of a wearable device 410 through a communication interface in the smartphone 400. The processor may output an image 420 to a display of the smartphone 400 to guide the user such that the rear surface of the main body of the wearable device faces upward so as to measure the first force, or output an image (not shown) to guide the user such that the rear surface of the main body of the wearable device faces downward so as to measure the second force. The processor of the smartphone 400 may provide the guide using various methods using a sound output device or a haptic device, but the present disclosure is not limited thereto.

Then, the processor 130 may calibrate the force sensor based on at least one of the measured first force and second force. In this case, the processor 130 may perform a calibration each time, for example, at the user's request, at a predetermined interval, or before estimation of blood pressure.

The processor 130 may guide the user to re-measure a force or to inspect the wearable device when at least one of the first force or the second force, or a statistical value of the first force and the second force is outside a preset reference range. Here, the preset reference range may be a specific reference range that reflects characteristics of the sensor, and may be determined, for example, based on a force obtained in the factory calibration by a manufacturer of the wearable device. For example, the processor 130 may compare each of the measured first and second forces with each of the forces obtained when the rear surface of the main body faces upward and downward at the time of the factory calibration. When the comparison result is outside a predetermined reference range (e.g., within 10% of an initial value obtained at the time of the factory calibration or an initial value updated by a subsequent calibration), the processor 130 may guide the user to re-measure a force or to inspect the device. In this case, the predetermined reference range may be set for each or either of the first force and the second force.

Also, the processor 130 may compare the statistical value (e.g., average value) of the first force and the second force with a preset reference range (e.g., within 10% of an initial value obtained at the time of the factory calibration or an initial value updated by a subsequent calibration). The method of using the first force and the second force is not limited thereto. In addition, when the comparison result is outside the preset reference range, the processor 130 may guide the user to re-measure a force or inform the user that the inspection of the force sensor 120 is necessary. Also, when the number of times of the re-measurement exceeds a predetermined number of times, the processor 130 may inform the user that the inspection is necessary.

Meanwhile, when at least one of the first force and the second force or the statistical value of the first force and the second force is not outside the preset reference range, the processor 130 may use a preset initial value or may update the initial value to at least one of the first force and the second force or the statistical value of the first value and the second value. For example, when the measured first and second forces or the statistical value thereof is not outside the preset reference range, the processor 130 may determine that the force sensor 120 is normal and may continue to use a preset initial value, or may update the initial value to the measured first force, the measured second force, or the statistical value of the measured first and second forces and use the updated initial value.

According to another exemplary embodiment, the processor 130 may calibrate the force sensor 120 using a charging dock of the wearable device 100. For example, when the wearable device is connected to a wireless charging dock, the processor 130 may consider that as much force as the coupling force between a permanent magnet in the wearable device and a permanent magnet in the wireless charging dock is applied, and may calibrate the force sensor 120. In this case, a magnetic field may be adjusted by adjusting a current (e.g., alternating current) flowing inside the wireless charging dock. Thus, the magnitude of the coupling force may be adjusted.

First, the processor 130 may guide the user to connect the charging dock to the force sensor 120. For example, the processor 130 may output an image of the charging dock being connected to the force sensor through the display device 230 of the output interface. FIG. 5 is a diagram illustrating an example of providing guide in the form of an image to connect a wearable device and a charging dock. An image 510 of FIG. 5 shows that a charging dock 500 is connected to a wearable device while a main body is turned over such that a rear surface 300 of a main body on which a force sensor is disposed faces upward. The user may connect the wearable device and the charging dock 500 according to the guide in the form of an image, and thus the force sensor 120 may measure a force. In this case, in order to increase the accuracy of measurement of force by excluding other forces, accessories of the wearable device, for example, a watch case, a strap, and other accessories connected to the main body, may be removed, and the processor 130 may additionally guide the removal of such accessories.

According to an exemplary embodiment, the main body 210 may further include a control circuit (e.g. the control circuit 141 illustrated in FIG. 1) configured to control the current in the charging dock. For example, the control circuit may adjust an alternating current flowing in the wireless charging dock to a plurality of levels and form a magnetic field for each level. Thus, the force corresponding to the coupling force between the wearable device and a permanent magnet may be measured for each level. When the wearable device and the wireless charging dock are connected, the control circuit may be controlled manually by the user. When the connection is detected, the control circuit may automatically control the alternating current.

Meanwhile, the processor 130 may provide the guide using various methods, such as text messages, voice signals, haptic signals, and the like, as well as the method of using the image through the display device 230. For example, the processor 130 may output a text message or a voice message, such as "Please connect the wireless charging dock and the watch" or the like, through the display device 230 of the wearable device. In addition, the processor 130 may provide guide together with a haptic signal, for example, by outputting an image of connecting the wearable device and the wireless charging dock after vibration.

In addition, the processor 130 may guide the user to connect the charging dock to the force sensor using a display or a sound output device of another wirelessly connected device.

Figure 6:
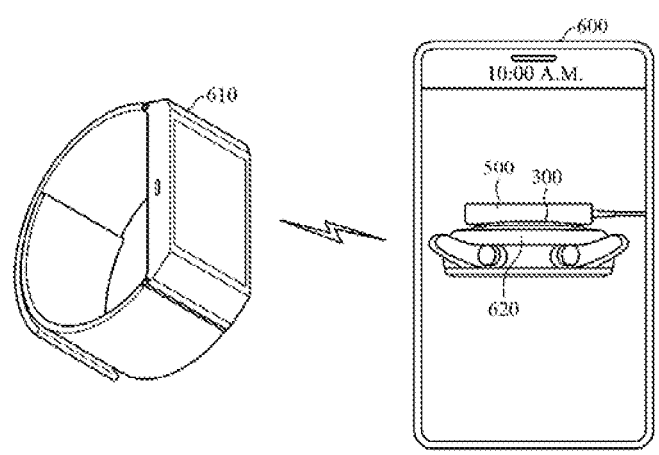
FIG. 6 is a diagram illustrating an example of provide guide via a combination of a wearable device and a smartphone according to another exemplary embodiment.

FIG. 6 is a diagram illustrating an example of providing guide via a combination of a wearable device and a smartphone according to an exemplary embodiment. Referring to FIG. 6, a processor may be mounted in a main body of a smartphone 600. Upon receiving a calibration request, the processor of the smartphone 600 may communicate with a communication interface included in the main body of a wearable device 410 through a communication interface in the smartphone 600. Also, the processor may output an image 620 of a charging dock being connected to a force sensor to a display of the smartphone 600. The processor of the smartphone 600 may provide guide using various methods using a sound output device or a haptic device, but the present disclosure is not limited thereto.

Then, the processor 130 may calibrate the force sensor based on a force measured according to the change in current after the charging dock is connected. For example, the processor 130 may calibrate the force sensor based on the force measured for each level of a current according to the current adjusted stepwise to a plurality of levels by a control circuit.

For example, when at least one of the forces which are measured for each of the plurality of levels according to the change in the current, or a statistical value of a plurality of forces, is outside a preset reference range, the processor 130 may guide the user to re-measure a force or to inspect the wearable device. Here, the preset reference range may be a specific reference range that reflects characteristics of the sensor, and may be determined, for example, based on a force obtained in the factory calibration by a manufacturer of the wearable device. For example, the processor 130 may compare the force measured for each level of the current with a force obtained for each level of a current at the time of the factory calibration. When the comparison result is outside a predetermined reference range (e.g., within 10% of an initial value obtained at the time of factory calibration or an initial value updated by a subsequent calibration), the processor 130 may guide the user to re-measure a force or to inspect the device. Also, the processor 130 may compare the statistical value (e.g., average value) of the forces for each of the levels of the current, which are measured according to the change in the current, with a preset reference range (e.g., within 10% of an initial value obtained at the time of the factory calibration or an initial value updated by a subsequent calibration). The method of using the forces measured for each level of the current is not limited thereto. In addition, when the comparison result is outside the preset reference range, the processor 130 may guide the user to re-measure a force or inform the user that the inspection of the force sensor 120 is necessary. Also, when the number of times of the re-measurement exceeds a predetermined number of times, the processor 130 may inform the user that the inspection is necessary.

Further, when at least one of the plurality of forces measured according to the change in the current, or a statistical value of the plurality of forces, is not outside the preset reference range, the processor 130 may use a preset initial value or may update the initial value to at least one of the plurality of forces measured according to the change in the current, or to a statistical value of the plurality of forces. For example, when the force measured for each level of the current or the statistical value of the forces is not outside the preset reference range, the processor 130 may determine that the force sensor 120 is normal and may continue to use a preset initial value, or may update the initial value to the force measured for each level of the current or the statistical value of the forces and use the updated initial value.

Figure 7:
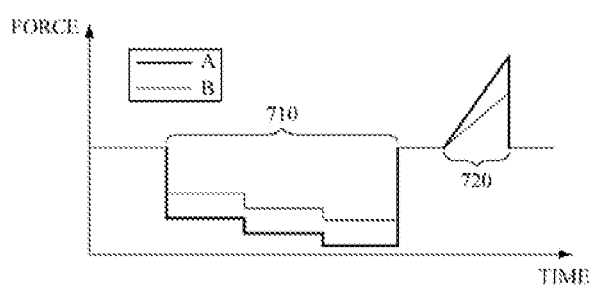
FIG. 7 is a graph illustrating a force over time measured by a force sensor according to an exemplary embodiment.

FIG. 7 is a graph illustrating a force over time measured by a force sensor according to an exemplary embodiment. Assuming that force sensor A deforms more than force sensor B, when the intensity of current is reduced stepwise over time in a calibration operation 710, it can be seen that an amount of change over time in the force sensor A is greater than an amount of change over time in the force sensor B. Also, it can be seen that an amount of change over time in the force sensor A is greater than an amount of change over time in the force sensor B even in a measurement operation 720. Accordingly, it can be anticipated that the degree of calibration of the force sensor A subjected to large deformation would be greater than the degree of calibration of the force sensor B when an estimated value of the force of the measurement operation 720 is determined based on the force of the calibration operation 710.

Meanwhile, the processor 130 may guide the user such that the rear surface of the main body faces upward while the charging dock is not connected, and may calibrate the force sensor based on a first force measured according to the guide and a force measured according to the change in current. That is, the accuracy of calibration may be improved by additionally using the force obtained when the charging dock is not connected, together with the force for each level of the current, which is measured according to the adjusted current.

When a contact force and a pulse wave signal are measured by the force sensor and the pulse wave sensor, respectively, at the time of estimating blood pressure, the processor 130 may estimate blood pressure based on the measured contact force and pulse wave signal. For example, the processor 130 may obtain an oscillometric envelope based on the contact force and the pulse wave signal, and estimate blood pressure based on the obtained oscillometric envelope.

In this case, the processor 130 may determine that the contact force is a value obtained by subtracting an initial value set according to calibration from the contact force measured at the time of estimating blood pressure. For example, when a first force and a second force that are measured according to guide is not outside a preset reference range, an initial value may be updated to the first force or the second force, and the contact force may be determined by subtracting the updated initial value from the contact force measured at the time of estimating blood pressure.

Figure 8A:
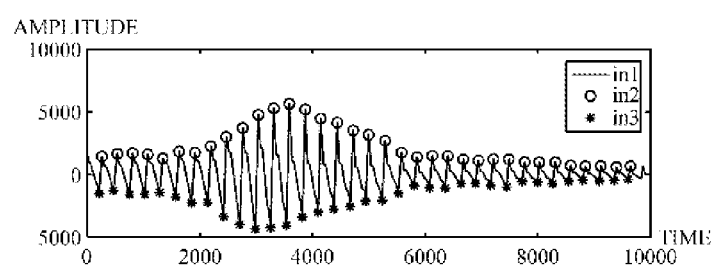
FIGS. 8A and 8B are graphs for estimating blood pressure using an oscillometric envelope according to an exemplary embodiment.
Figure 8B:
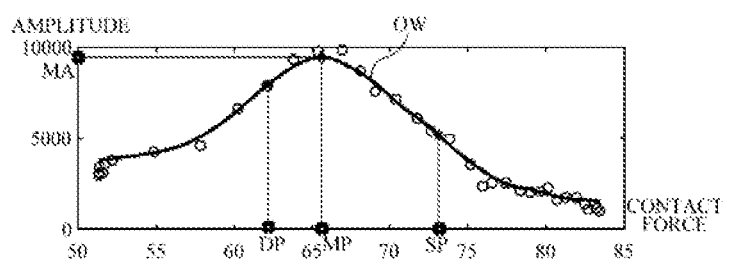

FIG. 8A illustrates the change in amplitude of a pulse wave signal (e.g., PPG signal) when an object in contact with the pulse wave sensor 110 gradually increases pressing force. FIG. 8B depicts an oscillometric envelope OW representing the relationship between the change in contact force and the amplitude of a pulse wave signal.

For example, the processor 130 may extract a peak-to-peak point by subtracting an amplitude value in3 of a negative (−) point from an amplitude value in2 of a positive (+) point of a pulse wave signal waveform envelope in1 at each measurement time. Also, the processor 130 may obtain an oscillometric envelope OW by plotting a peak-to-peak amplitude based on a contact pressure value at the corresponding point in time, and performing, for example, polynomial curve fitting.

The processor 130 may estimate, for example, blood pressure by using the thus generated oscillometric envelope OW. The mean blood pressure may be estimated based on a contact pressure MP of a maximum point MA of the pulse wave in an oscillogram. For example, the contact pressure MP of the maximum point MA of the pulse wave may be determined as the mean blood pressure, or the mean blood pressure may be obtained from the contact pressure MP using a predefined mean blood pressure estimation equation. In this case, the mean blood pressure estimation equation may be defined as various linear or non-linear combination functions, such as addition, subtraction, division, multiplication, logarithmic value, regression equation, and the like, with no specific limitation.

In addition, the processor 130 may obtain, as a feature value, at least one of a contact pressure value at a maximum amplitude point of the oscillometric envelope and contact pressure values having predetermined proportions of the contact pressure value at the maximum amplitude point, and may estimate the blood pressure based on the obtained feature value. For example, the processor 130 may estimate diastolic blood pressure and systolic blood pressure by using contact pressure values DP and SP at points at which an amplitude has a value equal to a predetermined proportion (e.g., 0.5 to 0.7) of the amplitude value of the pulse wave maximum point MA in the left and right of the pulse wave maximum point. The contact pressure values DP and SP may be determined as the diastolic blood pressure and the systolic blood pressure, respectively, or the diastolic blood pressure and the systolic blood pressure may be estimated from the respective contact pressure values DP and SP by using a predefined diastolic blood pressure estimation equation and a predefined systolic blood pressure estimation equation.

Figure 9:
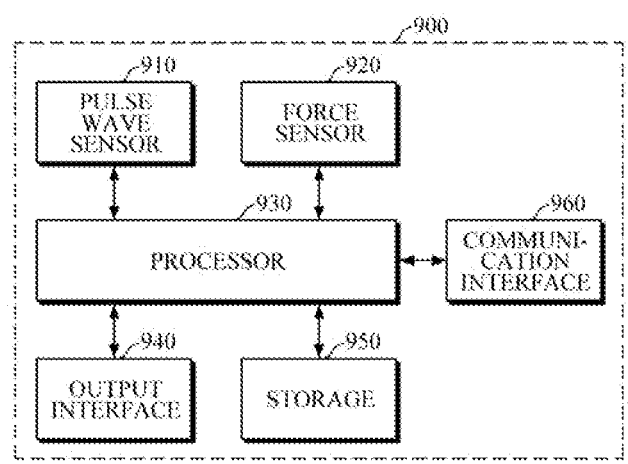
FIG. 9 is a block diagram illustrating a wearable device according to another exemplary embodiment.

FIG. 9 is a block diagram illustrating a wearable device according to another exemplary embodiment.

Referring to FIG. 9, a wearable device 900 may include a pulse wave sensor 910, a force sensor 920, a processor 930, an output interface 940, a storage 950, and a communication interface 960. The pulse wave sensor 910, the force sensor 920, and the processor 930 have been described in detail above, and thus descriptions thereof will not be reiterated.

The output interface 940 may output and provide a processing result of the processor 930 to the user. For example, the processing result may be provided to the user using a visual output module, such as a display, a sound output module, such as a speaker, or a haptic module that provides information through, for example, vibration or tactile sensation. In addition, the processor 930 may monitor a user's health condition on the basis of a blood pressure estimation result. The output interface 940 may output warning when a risk of the health condition is expected.

The storage 950 may store a variety of reference information necessary for blood pressure estimation or a processing result of the processor 930. For example, the reference information may include information regarding driving conditions for a light source, a blood pressure estimation model, and the like.

The storage 950 may include at least one type of storage medium of a flash memory type, a hard disk type, a multimedia card micro type, a card type memory (for example, secure digital (SD) or extreme digital (XD) memory), a random access memory (RAM), a static random access memory (SRAM), a read-only memory (ROM), an electrically erasable programmable read-only memory (EE-PROM), a programmable read-only memory (PROM), a magnetic memory, a magnetic disk, and an optical disk, but is not limited thereto.

The communication interface 960 may communicate with an external device to transmit and receive data related to blood pressure estimation. In this case, the external device may include a user's portable device, such as a smartphone, a tablet PC, a desktop computer, a notebook computer, or the like, and a device of a professional medical institution. The communicator 960 may use Bluetooth communication, Bluetooth low energy (BLE) communication, near field communication unit, wireless local access network (WLAN) communication, Zigbee communication, infrared data association (IrDA) communication, Wi-Fi direct (WFD) communication, ultra wideband (UWB) communication, Ant+ communication, Wi-Fi communication, and 3G, 4G, and 5G communication technologies. However, the communication technologies for use are not limited thereto.

Figure 10:
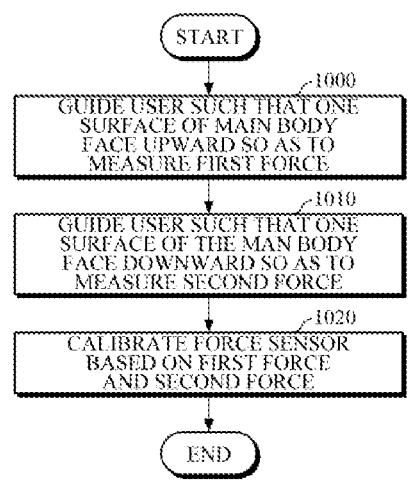
FIGS. 10 and 11 are flowcharts illustrating a method of calibrating a force sensor according to an exemplary embodiment.

FIG. 10 is a flowchart illustrating a method of calibrating a force sensor in a wearable device according to an exemplary embodiment. The calibration of a force sensor has been described above in detail, and thus will be briefly described below to prevent redundancy.

Referring to FIG. 10, a wearable device may guide a user such that one surface of a main body faces upward so as to measure a first force in operation 1000. For example, the wearable device may output an image of a main body with one surface facing upward so that a force sensor measures the first force.

Then, the wearable device may guide the user such that one surface of the main body faces downward so as to measure a second force in operation 1010. For example, the wearable device may output an image of the main body with one surface facing downward so that the force sensor measures the second force.

In addition, the wearable device may guide the user such that one surface of the main body faces upward so as to measure the first force, and guide the user such that one surface of the main body faces downward so as to measure the second force by using a display or a sound output device of another device wirelessly connected to the wearable device.

Then, the wearable device may calibrate the force sensor based on at least one of the measured first and second forces in operation 1020. In this case, the wearable device may perform a calibration each time, for example, at the user's request, at a predetermined interval, or before estimation of blood pressure.

The wearable device may guide the user to re-measure a force or to inspect the wearable device when at least one of the first force or the second force, or a statistical value of the first force and the second force is outside a preset reference range. In addition, when at least one of the first force and the second force or the statistical value of the first force and the second force is not outside the preset reference range, the wearable device may use a preset initial value intact or may update the initial value to at least one of the first force and the second force or the statistical value of the first value and the second value.

Figure 11:
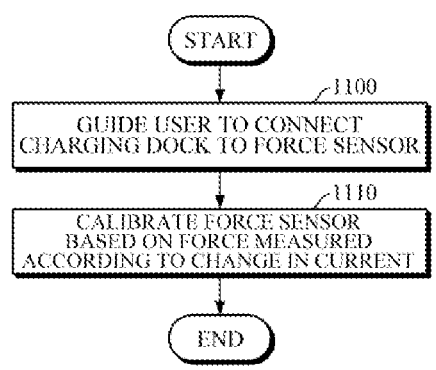

FIG. 11 is a flowchart illustrating a method of calibrating a force sensor in a wearable device according to another exemplary embodiment. The calibration of a force sensor has been described above in detail, and thus will be briefly described below to prevent redundancy.

First, the wearable device may guide the user to connect a charging dock to a force sensor in operation 1100. For example, the wearable device may output an image of the charging dock being connected to the force sensor, or guide the user to connect the charging dock to the force sensor by using a display or a sound output device of another device wireless connected to the wearable device.

Then, the wearable device may calibrate the force sensor based on the force measured according to the change in current after connection in operation 1110. The wearable device may calibrate the force sensor based on the force measured for each level of a current according to the current adjusted stepwise to a plurality of levels by a control circuit.

When at least one of the forces which are measured according to the change in the current, or a statistical value of a plurality of forces, is outside a preset reference range, the wearable device may guide the user to re-measure a force or to inspect the wearable device. In addition, when at least one of the forces which are measured according to the change in the current, or the statistical value of a plurality of forces, is not outside the preset reference range, the wearable device may use a preset initial value intact or may update the initial value to at least one of the forces which are measured according to the change in the current, or the statistical value of a plurality of forces.

The current embodiments can be implemented as computer readable codes in a computer readable record medium. Codes and code segments constituting the computer program can be easily inferred by a skilled computer programmer in the art. The computer readable record medium includes all types of record media in which computer readable data are stored. Examples of the computer readable record medium include a ROM, a RAM, a CD-ROM, a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wearable device comprising:
   a main body;
   a force sensor disposed on one surface of the main body and configured to measure a force; and
   a processor configured to control the force sensor to measure a first force when the one surface of the main body faces upwards, control the force sensor to measure a second force when the one surface of the main body faces downward, and calibrate the force sensor based on at least one of the measured first force and the measured second force.

2. The wearable device of claim 1, further comprising a display configured to output a first image of the main body with the one surface facing upward, wherein the processor is further configured to control the force sensor to measure the first force while the first image is displayed.

3. The wearable device of claim 1, further comprising a display configured to output a second image of the main body with the one surface facing downward, wherein the processor is further configured to control the force sensor to measure the second force while the second image is displayed.

4. The wearable device of claim 1, wherein the processor is further configured to guide a user such that the one surface of the main body faces upward so as to measure the first force, and guide the user such that the one surface of the main body faces downward so as to measure the second force, by using a display or a speaker of another device wirelessly connected to the wearable device.

5. The wearable device of claim 1, wherein, when at least one of the first force and the second force, or a statistical value of the first force and the second force is outside a preset reference range, the processor is further configured to guide a user to re-measure the force or to inspect the wearable device.

6. The wearable device of claim 1, wherein, when at least one of the first force and the second force or a statistical value of the first force and the second force is not outside a preset reference range, the processor is further configured to use a preset initial value or update the initial value to at least one of the first force and the second force or the statistical value of the first force and the second force.

7. The wearable device of claim 1, wherein the main body further comprises a pulse wave sensor disposed on the one surface of the main body and configured to measure a pulse wave signal, and when a contact force and the pulse wave signal are measured by the force sensor and the pulse wave sensor, respectively, at a time of estimating blood pressure, the processor is further configured to estimate blood pressure based on the contact force and the pulse wave signal.

8. The wearable device of claim 7, wherein the processor is further configured to obtain an oscillometric envelope based on the contact force and the pulse wave signal and to estimate the blood pressure using the oscillometric envelope.

9. A wearable device comprising:
   a force sensor configured to measure a force; and
   a processor configured to control the force sensor to measure a first force value when the wearable device is connected to a charging dock, and calibrate the force sensor based on the first force value measured according to a change in current while the force sensor is connected to the charging dock.

10. The wearable device of claim 9, wherein the processor is further configured to control the force sensor to measure a second force value while the wearable device is not connected to the charging dock and a contact surface of the force sensor faces upward, and to calibrate the force sensor based on the first force value and the second force value.

11. The wearable device of claim 9, further comprising a display configured to output an image of the charging dock being connected to the wearable device.

12. The wearable device of claim 9, wherein the processor is further configured to guide a user to connect the charging dock to the wearable device by using a display or a speaker of another device wirelessly connected to the wearable device.

13. The wearable device of claim 9, further comprising a control circuit configured to control a current in the charging dock, and the processor is further configured to calibrate the force sensor based on a plurality of force values measured for each level of the current according to the current adjusted stepwise to a plurality of levels by the control circuit.

14. The wearable device of claim 9, wherein, when at least one of the plurality of force values which are measured according to the change in the current, or a statistical value of the plurality of force values, is outside a preset reference range, the processor is further configured to guide a user to re-measure the force or to inspect the wearable device.

15. The wearable device of claim 9, wherein, when at least one of a plurality of forces values measured according to the change in the current, or a statistical value of the plurality of force values, is not outside a preset reference range, the processor is further configured to use a preset initial value or update the preset initial value to at least one of the plurality of force values measured according to the change in the current, or to the statistical value of the plurality of force values.

16. The wearable device of claim 9, further comprises a pulse wave sensor configured to measure a pulse wave signal, and when a contact force and the pulse wave signal are measured by the force sensor and the pulse wave sensor, respectively, at a time of estimating blood pressure, the processor is further configured to estimate blood pressure based on the contact force and the pulse wave signal.

17. A method of calibrating a force sensor in a wearable device, the method comprising:

guiding a user to place one surface of a main body to face upwards when the force sensor measures a first force;

guiding the user to place the one surface of the main body to face downward when the force sensor measures a second force; and calibrating the force sensor based on at least one of the measured first force and the measured second force.

18. The method of claim 17, wherein the guiding the user to place the one surface of the main body to face upwards comprises outputting an image of the main body with the one surface facing upward while the force sensor measures the first force.

19. The method of claim 17, wherein the guiding of the user to place the one surface of the main body to face downward comprises outputting an image of the main body with the one surface facing downward while the force sensor measures the second force.

20. The method of claim 17, wherein the calibrating of the force sensor comprises guiding the user to re-measure a force or to inspect the wearable device when at least one of the first force and the second force, or a statistical value of the first force and the second force, is outside a preset reference range.

* * * * *